US010570162B2

(12) United States Patent
Srivastava et al.

(10) Patent No.: US 10,570,162 B2
(45) Date of Patent: Feb. 25, 2020

(54) HIGH REFRACTIVE INDEX SILOXANES

(71) Applicant: Momentive Performance Materials Inc., Waterford, NY (US)

(72) Inventors: Rajiv Srivastava, Glenmont, NY (US); Douglas M. Dukes, Troy, NY (US)

(73) Assignee: Momentive Performace Materials Inc., Waterford, NY (US)

( * ) Notice: Subject to any disclaimer, the term of this patent is extended or adjusted under 35 U.S.C. 154(b) by 0 days.

(21) Appl. No.: 15/912,627

(22) Filed: Mar. 6, 2018

(65) Prior Publication Data

US 2018/0194785 A1    Jul. 12, 2018

Related U.S. Application Data

(63) Continuation of application No. 14/774,871, filed as application No. PCT/US2014/027617 on Mar. 14, 2014, now Pat. No. 9,963,469.

(60) Provisional application No. 61/782,138, filed on Mar. 14, 2013.

(51) Int. Cl.
| | |
|---|---|
| *C08G 77/38* | (2006.01) |
| *C07F 7/08* | (2006.01) |
| *C08G 77/20* | (2006.01) |
| *A61Q 1/02* | (2006.01) |
| *A61Q 19/00* | (2006.01) |
| *A61K 8/891* | (2006.01) |
| *A61K 8/895* | (2006.01) |
| *A61K 8/58* | (2006.01) |
| *C08G 77/04* | (2006.01) |
| *A61Q 1/00* | (2006.01) |
| *A61Q 1/06* | (2006.01) |
| *C08G 77/398* | (2006.01) |
| *C08G 77/14* | (2006.01) |
| *C08G 77/26* | (2006.01) |
| *C08G 77/28* | (2006.01) |
| *C08G 77/12* | (2006.01) |

(52) U.S. Cl.
CPC ............ *C07F 7/0838* (2013.01); *A61K 8/585* (2013.01); *A61K 8/891* (2013.01); *A61K 8/895* (2013.01); *A61Q 1/00* (2013.01); *A61Q 1/02* (2013.01); *A61Q 1/06* (2013.01); *A61Q 19/00* (2013.01); *C08G 77/04* (2013.01); *C08G 77/045* (2013.01); *C08G 77/20* (2013.01); *C08G 77/38* (2013.01); *C08G 77/398* (2013.01); *A61K 2800/26* (2013.01); *C08G 77/12* (2013.01); *C08G 77/14* (2013.01); *C08G 77/26* (2013.01); *C08G 77/28* (2013.01)

(58) Field of Classification Search
CPC ...... C08G 77/38; C08G 77/398; C08G 77/14; C08G 77/26; C08G 77/28
See application file for complete search history.

(56) References Cited

U.S. PATENT DOCUMENTS

| | | |
|---|---|---|
| 4,100,172 A | 7/1978 | Mui |
| 4,598,135 A | 7/1986 | Buese |
| 4,640,968 A | 2/1987 | Watanabe et al. |
| 4,642,356 A | 2/1987 | Langner et al. |
| 4,675,372 A | 6/1987 | Policastro |
| 4,900,779 A | 2/1990 | Leibfried |
| 5,725,790 A | 3/1998 | Osawa et al. |
| 6,268,456 B1 | 7/2001 | Gregorovich |
| 6,507,049 B1 | 1/2003 | Yeager et al. |
| 6,531,260 B2 | 3/2003 | Iwasawa et al. |
| 6,911,518 B2 | 6/2005 | Lichtenhan et al. |
| 7,009,031 B2 | 3/2006 | Toshimura et al. |
| 7,777,064 B2 | 8/2010 | Mizori |
| 7,879,405 B2 * | 2/2011 | Kaji ................. C08L 83/06 427/387 |
| 89,116,671 | 12/2014 | Ko et al. |
| 2001/0026789 A1 | 10/2001 | Herve et al. |
| 2003/0016681 A1 | 1/2003 | Lampola |
| 2003/0212233 A1 | 11/2003 | Angeletakis et al. |
| 2003/0224286 A1 | 12/2003 | Barclay et al. |
| 2007/0073026 A1 | 3/2007 | Miyoshi |
| 2007/0225433 A1 | 9/2007 | Arai |
| 2008/0015326 A1 | 1/2008 | Kodama et al. |
| 2009/0137764 A1 | 5/2009 | Sutton et al. |
| 2009/0309121 A1 | 12/2009 | Ito |
| 2011/0301247 A1 | 12/2011 | Hayakawa |

(Continued)

FOREIGN PATENT DOCUMENTS

| | | |
|---|---|---|
| EP | 0179355 | 4/1986 |
| EP | 0712855 | 5/1996 |
| EP | 2444062 | 4/2012 |
| JP | 361-015887 | 1/1986 |
| JP | S61-106585 | 5/1986 |
| JP | H08-225582 | 9/1996 |
| JP | H09-194596 | 7/1997 |

(Continued)

OTHER PUBLICATIONS

J. V. Crivello and G. Lohden, "Preparation of 1-Propenyl Ether Functional Siloxanes by Chemoselective Hydrosilation and Their Cationic Photopolymerization," Macromolecules 1995, v.28, pp. 8057-8064.

Yu. V. Khoroshavina and G. A. Nikolaev, "1, 3, 5-Trimethyl-1, 3, 5-tris(hexafluoroalkyl)cyclotrisiloxanes: Basicity of Ethoxysilanes and Cyclosiloxanes," Russian Journal of General Chemistry 2011, v.81, pp. 690-693.

(Continued)

*Primary Examiner* — Margaret G Moore
(74) *Attorney, Agent, or Firm* — Joseph Waters; McDonald Hopkins LLC

(57) ABSTRACT

A polymer material comprising a constraint bicyclic bridged structure such as bicyclo(2,2,1) ring system, most preferably a norbornyl group, pendant to a siloxane backbone. The bridged bicyclic-containing materials can exhibit good refractive index, transparency, gas permeability, and/or other properties making them suitable for use in a variety of applications.

21 Claims, No Drawings

(56) References Cited

U.S. PATENT DOCUMENTS

2012/0130041 A1* 5/2012 Han .................. C08G 65/4012
528/125

FOREIGN PATENT DOCUMENTS

| JP | H11-507091 | 6/1999 |
| JP | 2001-039846 | 2/2001 |
| JP | 2002-128788 | 5/2002 |
| JP | 2003-261783 | 9/2003 |
| JP | 2004-038142 | 2/2004 |
| JP | 2006-063234 | 3/2006 |
| JP | 2007-246602 | 9/2007 |
| JP | 2008-069210 | 3/2008 |
| JP | 2008-138146 | 6/2008 |
| JP | 2008138146 | 6/2008 |
| JP | 2009-501837 | 1/2009 |
| JP | 2009-081430 | 4/2009 |
| JP | 2011-111523 | 6/2011 |
| JP | 2011-236207 | 11/2011 |
| JP | 2012-017317 | 1/2012 |
| KR | 2012-0110301 | 10/2012 |
| WO | 9639468 | 12/1996 |
| WO | 2007100329 | 9/2007 |
| WO | 2008-082128 | * 7/2008 |
| WO | 2008082128 | 7/2008 |
| WO | 2008/082128 | 8/2008 |
| WO | 2012040457 | 3/2012 |

OTHER PUBLICATIONS

ISA/US, International Search Report and Written Opinion for PCT/US2014/027617, dated Sep. 16, 2014.
Supplementary European Search Report for Application 14770085.0, dated Jul. 15, 2016, 9 pgs., European Patent Office, Germany.

* cited by examiner

HIGH REFRACTIVE INDEX SILOXANES

REFERENCE TO RELATED APPLICATIONS

The present application is a continuation of U.S. application Ser. No. 14/774,871 filed on Sep. 11, 2015, now U.S. Pat. No. 9,963,469 which claims priority to and benefit of PCT Application No. PCT/US2014/027617 filed on Mar. 14, 2014, which claims priority to and benefit of U.S. Provisional Application No. 61/782,138 filed on Mar. 14, 2013, each of which is incorporated herein by reference in its entirety.

FIELD

The present technology relates to silicone materials, and particularly to a modified silicone material that contains a bridged bicyclic structure, such as a bicyclo(2,2,1) ring system bonded to a silicon atom. The modified silicon-containing molecules and polymer can exhibit excellent properties such that they can be used in a variety of applications including, but not limited to, a coating, contact lenses, intraocular lenses, solid state lighting (light emitting diodes, organic light emitting diodes, laser diodes), waveguides (both planar and "fiber" geometries), optical computing, optical storage media, antireflection coatings, conformal coatings, optical lenses, micro lenses, automobile topcoats, paint formulations, hair care products, gradient refractive index optical components, and dynamic gradient refractive index components.

BACKGROUND

Siloxane polymers or copolymers having a high refractive index have been increasingly used for a variety of optical applications including, for example, in contact lenses, intraocular lenses, etc. Such polymers are also finding their way into other optical applications requiring high transmission and high refractive index including but not limited to, solid state lighting (light emitting diodes, organic light emitting diodes, laser diodes), waveguides (both planar and "fiber" geometries), optical computing, optical storage media, antireflection coatings, conformal coatings, optical lenses, micro lenses, automobile topcoats, paint formulations, hair care products, gradient refractive index optical components, dynamic gradient refractive index components, etc.

Depending on the application, the polymers and products formed from such polymers may need to exhibit a wide range of properties including sufficient structural integrity, strength, elasticity and elongation, and index of refraction. In some applications, the polymers must exhibit these properties when formed into a thin film. For example, in intraocular lenses, the lens must be thin and pliable for insertion through a small incision in intraocular lens applications, be able to regain its original shape after incision, and have sufficient structural integrity and strength to retain such shape under normal use conditions.

Typical optical grade methyl siloxanes have excellent optical transmission, but intrinsically low refractive index (1.41) and poor barrier properties against moisture and gas. The development of higher refractive index siloxanes with improved barrier properties has revolved around the use of cyclohexyl, cyclopentyl, and phenyl groups to increase the refractive index beyond 1.40. Examples of typical optical grade siloxanes include a copolymer of cyclohexylmethyl-dimethyl siloxanes, cyclopentylmethyl-dimethyl siloxanes, diphenyl-dimethyl siloxanes, or methylphenyl-dimethyl siloxanes.

Aromatic groups are traditionally introduced into the siloxane polymers and conventional co-polymers to increase the refractive index of the materials. Most often these groups consist of dimethylsiloxane-phenylmethylsiloxane co-polymers or dimethylsiloxane-diphenylsiloxane co-polymers. At a phenyl content of approximately 15 mole %, a polydimethyl siloxane/methylphenyl siloxane co-polymer has a refractive index of 1.462.

The introduction of refractive index modifying groups, such as phenyl-groups, in polysiloxanes is known to result in several disadvantages. Materials formed from siloxanes containing phenyl groups can have reduced flexibility, poor mechanical strength and elasticity, and they may be hard and brittle. Further, materials with phenyl content greater than 40 wt % are not easily processed and tend to exhibit poor mechanical strength. This limits the refractive index that can be achieved to about 1.54. In addition, phenyl group containing polymers are known to be unstable in ultraviolet light.

The incorporation of phenyl into the silicones makes the resulting polymer more vulnerable under thermal and UV exposure conditions. This result in yellowing of the optical material and transmission losses such that the transmission level is below a tolerable level and can lead to mechanical failure of a device in the optical components. There is a need for high RI siloxanes that have low permeability to oxygen and have high survivability, which are demonstrated by the present invention.

SUMMARY

The present invention provides a modified silicon-containing material, methods of making the same, cured articles formed from such materials, and their utility in various applications. In one aspect, the invention provides silicon-containing materials in the form of silanes and siloxanes modified with a bridged bicyclic group, bonded to a silicon atom, such as bicyclo(2,2,1) group (Formula 1) where $R^1$-$R^7$ can be H, C1-C12 alkyls, —$CO_2$R', —$(CH_2)_n$—B where n=0-12, B=OR', SR', $NR^8R^9$, R'=C1-C12 alkyls, and $R^8$ and $R^9$ are unsubstituted or substituted monovalent hydrocarbon groups. The substituent at the bridge head position A is from $CH_2$, NR', S, SO, or $SO_2$. The modified silicone materials can be used to form articles that exhibit excellent mechanical and physical properties.

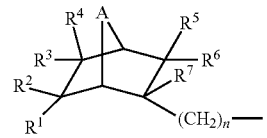

1

In one aspect, the present invention provides a modified siloxane polymer comprising a bicycle(2,2,1) group where R'—$R^7$ are hydrogen, and A is $CH_2$ group and n is 0. As used herein, and unless denoted otherwise, the term "a bicyclic group" will refer to a compound of Formula 1. Generally, the bicyclic group is attached to a silicon atom in the molecule.

In one aspect, the bicyclic-modified silicone material can be used to form a cured article. The article can exhibit excellent mechanical and/or physical properties including, but not limited to, relatively high refractive index, transparency, gas permeability, hardness, etc.

In another aspect, bicyclic-modified silanes are used as monomers toward polysiloxane synthesis of a variety of polymer and copolymer compositions and architectures.

In yet another aspect, a method of making the bicyclic-containing siloxanes, and the utility of these bicyclic-modified silanes and siloxanes are provided.

DETAILED DESCRIPTION

The present invention provides a modified silicone material comprising a bicyclic group. In one embodiment, the bicyclic group is a bicyclo(2,2,1) group of Formula 1 attached to a silicon atom in the material. The silicon-containing material can be, for example, a siloxane. In one embodiment, the bicyclic-modified silicone material comprises a cyclic siloxane. In another embodiment, the bicyclic-modified silicone is a straight-chained siloxane. In another embodiment, the bicyclic-modified silicon-containing molecule is a silane. The bicyclic-modified silicones can be used to form cured articles that can exhibit excellent mechanical and physical properties including, but not limited to, high refractive index, low gas permeability, high transparency, and long-term stability.

It is useful to describe generic molecular building blocks, and their formulas, to provide the basis for writing complex molecular structures. In each instance, the silicon atom is coordinated by four (4) bonds. Here, we will define the four general building block components of siloxanes as M, D, T, and Q units, listed in order of increasing number of Si—O bonds per unit. M-units have one Si—O bond and thus can be described by the formula: $R^{10}R^{11}R^{12}SiO_{1/2}$, where $R^{10}$, $R^{11}$, $R^{12}$ are independently selected organic groups bonded to the silicon atom through a C—Si bond. D-units have two Si—O bonds, and thus can be described by the formula: $R^{13}R^{14}SiO_{2/2}$, again, where $R^{13}$ and $R^{14}$ are independently selected organic groups bonded to the silicon atom through a C—Si bond. T-units have three Si—O bonds, and thus can be described by the formula: $R^{15}SiO_{3/2}$, where $R^{15}$ is a selected organic groups bonded to the silicon atom through a C—Si bond. Finally, Q-units have four Si—O bonds, and can be described by the formula: $SiO_{4/2}$. In this instance, silicon (Si) is coordinated only to the oxygen atoms. Using these four building blocks, descriptive polymer chemistries can be readily described using simple constructs. For example, $MD_XM$ is a linear siloxane fluid having two end-capping units (M) on either end of the linear siloxane units (D-units), with the number of repeat units indicated by the value of "x". A polymer can incorporate many building block units in a single molecule and as the functional groups $R^{10}$-$R^{15}$ change, as in the case of siloxane co-polymers, multiple building blocks of the same type are indicated by different superscripts in the notation. In the formula above, the $R^{10}$-$R^{15}$ groups are chosen from hydrogen, hydroxyl, or a group containing 1-30 carbon atoms chosen from a linear or branched alkyl group, a cycloalkyl group, a linear or branched alkoxy group, an alkylvinyl group (including allyl), a branched or linear alkenyl group, a cycloalkenyl group, a linear or branched alkynyl group, an aryl group, a substituted aryl group, a polynuclear aromatic group, amide, amino-groups, propyl-mercapto groups, glycidyl-containing groups, or a bicyclic group of Formula 1. It is also useful to describe not only the linear, branched, and resinous structures through this notation, but cyclic siloxanes can also be described by having the absence of M groups on what would otherwise be a linear structure (D units). Thus, $D_4$ is a cyclic siloxane containing 4 repeat units.

Generally, the bicyclic-modified cyclo-siloxanes can be described by Formula 2:

(2)

where $D^{1-3}$ are various D units (as described above) and $R^{13}$ and $R^{14}$ of the D units are independently chosen from a bicyclic compound of Formula 1, methyl, H, or phenyl, where at least one of the $R^{13}$ or $R^{14}$ group is a bicyclic compound of Formula 1, each subscript a, b and c is an integer from 0 to 10 with the provision that a+b+c is from 3 to 10, and at least one of a, b, or c is greater than zero.

In one embodiment, the modified silicone material is a cyclic siloxane of the Formula 2a:

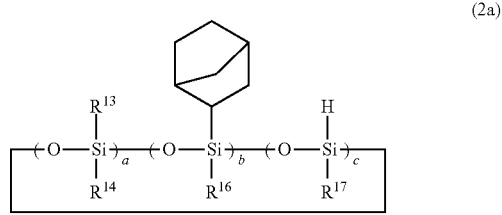

(2a)

where a is 0-6, and b is 1-6, and c is 0-6. In one embodiment, the polymer is a cyclic siloxane of Formula 2 where a is 0, b is 1-6, c is 0, and $R^{16}$ is methyl groups (formula 2b).

In one embodiment the polymer is a cyclic siloxane of formula 2 where a is 0, b is 1-4, c is 1-3, and $R^{16-17}$ are methyl groups (formula 2c). In these and other embodiments of cyclic siloxanes, a+b+c are from 3 to 10, more particularly from 3 to 8, even more particularly from 3 to 6.

As described above, the bicyclic-containing siloxane can be either a linear or branched, or even resinous polymer. Generally, the high refractive index polymer can be described containing any of the previously described M, D, T, and Q units. Thus, polymers containing the bicyclic compound of Formula 1 are of the general structure of Formula 3:

(3)

where each monomer unit ($M^1$, $M^2$, $D^1$, $D^2$, etc.) have independently selected $R^{10}$-$R^{17}$ groups, which are chosen from hydrogen, hydroxyl, a linear or branched alkyl group, an alcohol, a linear or branched alkoxy group, an aryl group, an alkylvinyl group, amide, amino-groups, acryloyl groups, carbonyl groups, silyloxy (e.g., alkoxy silane) groups, isocyanyl groups, mercapto groups (e.g., mercaptopropyl), epoxy-containing (e.g., glycidyl) groups, or a bicyclic group of Formula 1, where at least one $R^{10-17}$ group (irrespective of M, D, T, and Q units) is a bicyclic molecule of Formula 1; a is from 0-1000, b is from 0-500, c is from 0-500, d is from 0-100, e is from 0-100, f is from 0-100, g is from 0-1000, h is from 0-1000, and i is from 0 to 200, where at least two subscripts on any particular embodiment are positive integers.

In one embodiment, a high refractive index siloxane polymer may be described by linear or resinous variants of Formula 3 including, but not limited to:

$$MD^\dagger_b D^H_c T_e Q_g M,$$

$$M^H D_a D^\dagger_b D^H_c D^{Ph}_d T_e Q_g M^H,$$

$$MD_a D^\dagger_b D^{vi}_j T_e Q_g M,$$

$$M^H D_a D^\dagger_b D^{Ph}_d D^{vi}_j T_e Q_g M^H,$$

$$M^{vi} D_a D^\dagger_b D^{vi}_j T^\dagger_f Q_g M^{vi},$$

$$M^h D_a D^\dagger_b T_e Q_g$$

$$M_i T_e T^\dagger_f Q_g,$$

$$M_i D^\dagger_b T_e Q_g, \text{ or}$$

$$M_h M^\dagger_i D_a T_e Q_g,$$

where M, D, T, and Q are described above. In the above embodiments, "vi" represents a vinyl group, "†" represents a high refractive index molecule of Formula 1, M$^{vi}$ represents a dialkylvinylmonosiloxy, D$^\dagger$ represents monomer unit containing a bicyclic compound, where one or both of the R$^{13}$ and R$^{14}$ groups is a bicyclic compound of Formula 1, D$^H$ represents an alkyl hydrogen siloxy, D$^{vi}$ represents alkylvinylsiloxy. In still another embodiment, the siloxane polymer may be chosen from an MQ, MT, MDT, MDQ, MDTQ, TQ, DT, or DQ resin, where the resin comprises a T$^\dagger$ unit, a M$^\dagger$ unit, a D$^\dagger$ unit, or a combination of two or more thereof. In one embodiment, the † group can be a norbornyl group. The degree of polymerization of the bicyclic-modified siloxane polymer is not particularly limited and can be selected as desired for a particular purpose or intended use. In one embodiment, the polymer can contain from 1 to about 10,000 repeating units. In one embodiment, a is from about 0 to about 2000, b is from about 0 to about 1000, c is from about 0 to about 1000, and d is from about 0 to about 1000, e and f are from about 0 to 100, g is from 0 to 50 and j is from 0 to 1000.

In one embodiment the modified silicone material is a resinous siloxane of the formula Si$^\dagger$O$_{3/2}$ (T$^\dagger$ resin).

In another embodiment the modified silicone material is a resinous siloxane of the formula M$^\dagger_l$M$^\dagger_i$T$^\dagger_f$ where $0<l+i\le3f$ and $f>0$.

In yet another embodiment the modified silicone material is a resinous siloxane of the formula M$^\dagger_j$Q$_g$ where $1\le4$ g.

In one embodiment, the modified silicone material is a linear siloxane of the Formula (4):

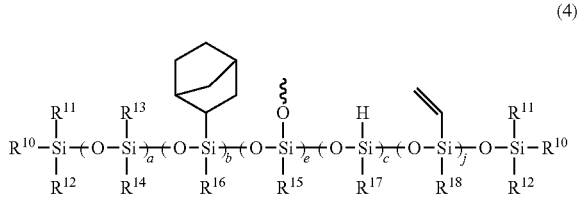

(4)

where R$^{10}$ groups are independently chosen from alkyl (e.g., methyl), vinyl, alkoxy, alcohol, hydride, halogen, mercapto (e.g., mercaptopropyl), amino, and epoxy (e.g., glycidyl alkyl) groups. R$^{11}$, R$^{12}$, R$^{13}$, R$^{14}$, R$^{15}$, R$^{17}$, and R$^{18}$ represent identical or different, unsubstituted or substituted monovalent hydrocarbon groups, aromatic groups, alkoxy, mercapto (e.g., mercaptopropyl), isocyanyl, amino, acryloyl, carbonyl, a silyloxy, e.g., alkoxy silane, and epoxy, e.g. glycidyl, groups. R$^{16}$ represents, independently, a bicyclic compound of Formula 1 or unsubstituted or substituted monovalent hydrocarbon groups. The numbers of various units (M, D, and T units) in formula 4 are positive integers and represented by a, b, c, e, and j. In one embodiment, the polymer of formula 4 is designed such that the "c" units and the "j" units are not present in the same polymer. That is, in one embodiment of formula 4, c is 0 when j is greater than 0, and j is 0 when c is greater than 0. The repeat units can further be sub classified into a', a", a''', etc., to accommodate higher order copolymers. The number of repeat units a is 0 to 1000, b is 1 to 500, c is 0 to 500, d is 0-500, z is 0-500. Examples of suitable hydrocarbon groups include, but are not limited to, methyl, propyl, octyl etc. Examples of suitable aromatic groups include, but are not limited to, phenyl, biphenyl, tolyl, benzyl, naphthyl, styryl, alpha-methyl styryl, anthryl, phenanthryl, etc. Suitable alkenyl groups include, but are not limited to, vinyl, allyl, vinylphenyl, allylphenyl, vinylbenzyl, allylbenzyl, etc.

In the present invention, the inclusion of the bicyclic-group into the siloxane material has been found to provide a silicone material that exhibits excellent properties when cured. The cured material can exhibit a relatively high refractive index especially as compared to conventional methyl siloxanes.

Unexpectedly, the bicyclic-modified siloxanes also limit the permeability of oxygen, providing an excellent barrier film compared to phenyl-siloxane systems, which is the current state of the art.

It will be appreciated that the siloxane polymers can also include other groups pendant to a silicon atom in the polymer chain to tune or adjust the properties of the polymer and articles formed therefrom. For example, as described above, the bicyclic-modified silicone material can include aromatic compounds attached to the silicon atoms in the material. The polymers can also include various cross-linking functionalities to introduce a variety of potential cure mechanisms. Such materials can be used to further adjust or tune the properties of the cured materials, e.g., the refractive index, and/or tune the manner in which they can be cured. Examples of suitable cure methods include, but are not limited to, addition cure (e.g., a vinyl reacting with a hydride), condensation cure, UV cure, thermal curing, etc. Other groups include, but are not limited to, epoxy-containing groups, alkoxy silicone-containing groups, thiol-containing groups, acrylate-containing groups, etc.

In one embodiment, the modified silicone material is of the Formula (5):

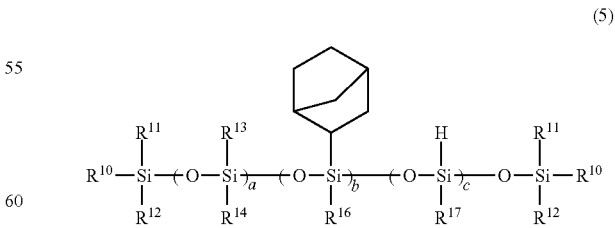

(5)

where R$^{10}$, R$^{11}$, R$^{12}$, R$^{13}$, R$^{14}$, R$^{16}$, R$^{17}$ are as described above, excluding the vinyl group. The repeat units a, b, and c can be as described above. In one embodiment, the modified silicone material is of the Formula 5, where R$^{10}$ is hydrogen.

In another embodiment the modified silicone material comprises an epoxy group. In one embodiment, the modified silicone material is of the formula 5, where the pendant Si—H is replaced by an epoxy group, such as in formula (5a)

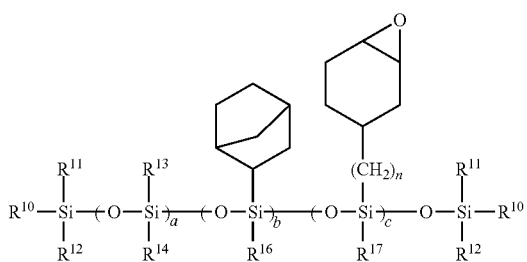

(5a)

In another embodiment the modified silicone material comprises a silyloxy group. In one embodiment, the modified silicone material is of the formula 5, where the pendant Si—H is replaced by a silyloxy group, such as in formula (5b)

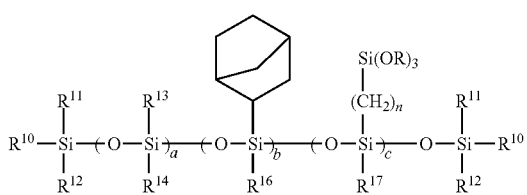

(5b)

In one embodiment, the bicyclic-modified silicone material is of the Formula (6):

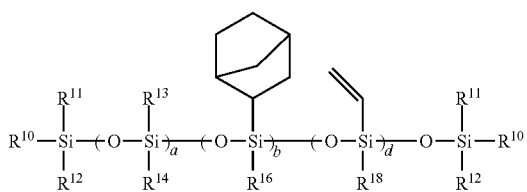

(6)

where $R^{10}$, $R^{11}$, $R^{12}$, $R^{13}$, $R^{14}$, $R^{16}$, $R^{18}$ are as described above, excluding hydrogen. The repeat units a, b, and j can be as described above. In one embodiment, the modified silicone material is of Formula 6, where $R^{10}$ is vinyl.

In one embodiment, the modified silicone material is of Formula (7):

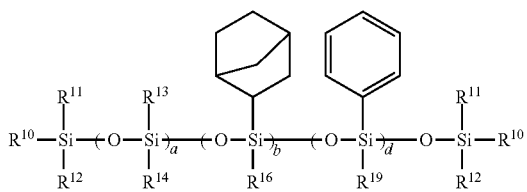

(7)

where $R^{10}$, $R^{11}$, $R^{12}$, $R^{13}$, $R^{14}$, $R^{16}$, are described above. $R^{19}$ can be phenyl or monovalent hydrocarbon. The repeat units a, b, and d are as described above. The repeat unit d is 0-500. In one embodiment, the bicyclic modified silicone material is of the Formula 7, where $R^{10}$ is vinyl (Formula (7a)). In another embodiment, the modified silicone material is of the Formula 7 where $R^{10}$ is hydrogen (Formula (7b)).

The bicyclic-compound content in the modified silicone material can be selected as desired for a particular purpose or intended use. The bicyclic content can be controlled or selected to allow the properties of the polymer (and subsequent articles) to be tuned. The modified polymer can have a bicyclic content of from about 90 wt % to about 1 wt % of the polymer; from about 70 wt % to about 20 wt % of the polymer, even from about 50 wt % to about 30 wt %, and even 40 wt % to 20 wt %. Here as elsewhere in the specification and claims, numerical values can be combined to form new or non-disclosed ranges.

In embodiments comprising aromatic groups attached to the bicyclic-modified silicone material, the aromatic content can be selected as desired to provide the modified silicone material and articles formed therefrom with desired properties. For example, aromatic groups can be included to improve refractive index. A large concentration of aromatic can, however, result in yellowing or a decrease in other properties of articles formed from such materials. In one embodiment, the modified polymer comprising bicyclic compounds has an aromatic content of about 40 wt % of the polymer or less; about 30 wt % of the polymer or less; about 20 wt % of the polymer or less; about 15 wt % of the polymer or less; about 10 wt % of the polymer or less; about 5 wt % of the polymer or less; even about 1 wt % of the polymer or less. In one embodiment, the bicyclic-modified polymer has bicyclic content from about 1 wt % to about 40 wt % of the polymer; from about 5 wt % to about 30 wt % of the polymer; from about 7 wt % to about 20 wt % of the polymer; even from about 10 to about 20 wt % of the polymer.

The bicyclic-modified siloxane materials can be prepared by any suitable process for attaching the bicyclic functionality to a siloxane. In one embodiment, the bicyclic-containing siloxane is formed by a hydrosilylation reaction of an unsaturated bicyclic compound, in this case norbornene, with a hydride functional cyclic siloxane or a hydride functional linear siloxane monomer or polymer. This can be carried out using a catalyst such as, for example, a platinum or rhodium based catalyst, with or without a suitable solvent, such as, for example, toluene. Examples of suitable reactions schemes for the hydrosilylation reaction are shown below:

Scheme 1

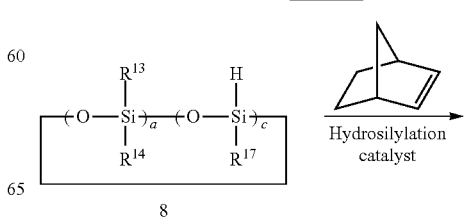

8

-continued

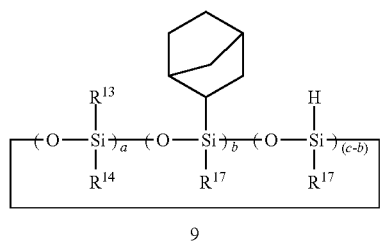

9

Scheme 2

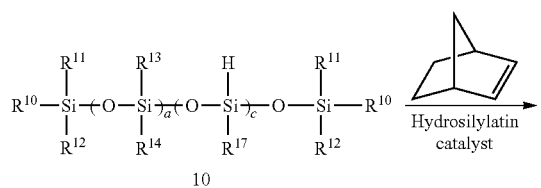

10

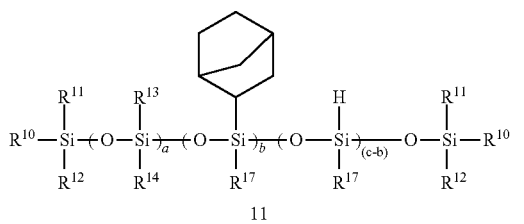

11

It will be appreciated that in the above reactions, the reaction can be controlled to replace any number of hydrides as desired to provide a particular material. In one embodiment, all the Si—H groups in the starting material are replaced by bicyclic groups. In another embodiment, only a fraction of the Si—H groups are replaced by bicyclic groups, leaving available Si—H bonds to further modify the polymer by adding other functional groups or for crosslinking.

In another embodiment, the bicyclic-containing material can be prepared by ring opening polymerization of a cyclic siloxane comprising a bicyclic functional group, for example, $D^†_4$ where $D^†$ is bicyclic-modified cyclosiloxane. The ring opening polymerization can be carried out via any suitable anionic or cationic ring opening polymerization process with the desired siloxane components or functionalities, generally described by $D_r$, where r is from 3 to 10 and the $R^{13}$ and $R^{14}$ groups are independently chosen from methyl, phenyl, hydrogen, or vinyl. These co-reactants include, but are not limited to, $D_3$, $D_4$, $D^{Ph}_4$, $D^{Ph2}_4$, $M^H D^H_c M^H$, $M^{vi} D^{vi}_j M^{vi}$, $MD_a D^{vi}_j M$ etc., where $D_4$ represents an alkyl cyclotetrasiloxane, $D^{Ph}_4$ represents a cyclotetrasiloxane comprising a phenyl group replacing an alkyl group on the Si atom, $D^{Ph2}_4$ represents a cyclotetrasiloxane comprising two phenyl groups attached to a Si atom, and $D_a$, $D^H_c$, $D^{vi}_j$, M, $M^H$, $M^{vi}$ represents various siloxanes monomers as described before. The repeat units a, c, and j are positive integers.

Examples of suitable routes to make various embodiments of bicyclic-containing materials (indicated by †) is shown in Scheme 3 (eq 1-3) below:

Scheme 3

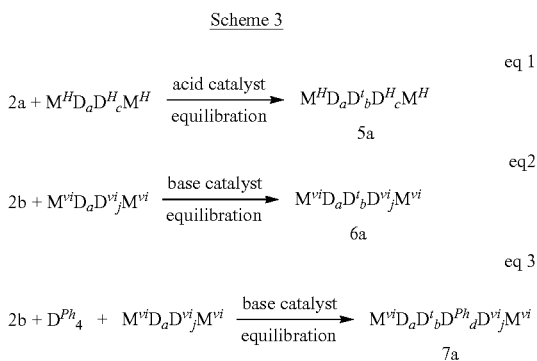

Although Scheme 3 illustrates routes to certain embodiments, it will be appreciated that the phenyl group can be replaced with any suitable substituent as desired to alter the polymer composition through any singular route provided above, or any non-limiting combination of the above routes.

Additionally, the bicyclic-containing siloxanes can also be prepared from monomers of bicyclic-containing small molecules. Such monomers can be made through the hydrosilylation of an unsaturated bicyclic compound, such as norbornene, to the appropriate choice of silanes, having the general formula $SiR^{20}_m X_n H_{(p-q)} N_q$, as shown in Scheme 4, formula 12:

Scheme 4

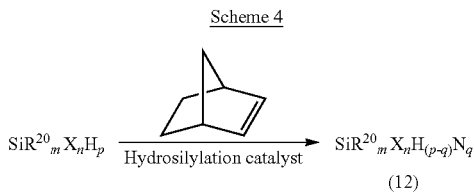

(12)

where $R^{20}$ is chosen from an alkyl, alkylvinyl, or aryl group, X is chosen from a halogen or alkoxy group, H is number of hydrogen attached to silicon, and N is the bicyclic group of Formula 1, shown as norbornene in this instance, $0 \leq m \leq 3$, $0 \leq n \leq 3$, $1 \leq p \leq 3$, $0 < q \leq p$, and m+n+p=4. Once produced, such bicyclic-modified silanes (monomers) can then lead to M, D, or T units in a bicyclic-modified siloxane polymer via any suitable condensation now known or later discovered for forming a siloxane polymer.

As described above, a modified silicone material can be prepared to provide a material having hydride groups, vinyl groups, or other suitable groups capable of undergoing reactions to allow for further modification of the silicone material with a desired functional group or to be used in crosslinking reactions. Thus, for example, a hydride such as the silicone material of Formula (5) can be reacted with an appropriate material to replace the Si—H group with a desired functional group such as, for example, the compounds of Formulas (5a), or (5b), or other desired functionalities. Alternatively, a desired material can be prepared directly without first preparing a partial hydride or vinyl-containing material by selection of appropriate starting materials with the desired functionalities.

While the siloxanes modified with a bridged bicyclic group may include hydride or vinyl groups to allow for crosslinking reactions, it will be appreciated that the modified siloxanes can include other groups, in addition to or in place of hydride or vinyl groups, to provide a material that can be used in crosslinking. That is, the M, D, or T units can be provided with a suitable functionality to allow for the material to be useful in crosslinking. Incorporating different functionalities allows for tuning the material to be useful in different types of curing reactions. Non-limiting examples of suitable crosslinking functionalities include epoxy, alkoxy, thiol, amino, isocyanyl, acryloyl, etc. Bicyclic modified siloxanes comprising an epoxy can be useful, for example, in thermal curing, photo curing, and amine curing reactions. Alkoxy, e.g., methoxy, or alkoxy silane functional materials can be used in condensation curing reaction using catalysts such as, but not limited to, tin-, titanium-, and/or bismuth-based catalysts. Thiol functional materials can be used in thermal curing or photo curing reactions when combined with suitable photo- or thermal-initiators now known or later discovered in the art.

Applications

The bicyclic-containing materials can be utilized in a variety of compositions and formulations that can be employed in numerous applications or end uses. In one embodiment, the bicyclic-containing materials can be utilized to form a cured article. A cured article can be formed by providing a composition comprising a bicyclic-containing material that contains reactive groups and a compound that will react with the bicyclic-containing compound. The compound that will react with the bicyclic-containing compound can be another bicyclic-containing compound of the same or of a different composition or structure. That is, in one embodiment, the bicyclic-containing compound can be provided as a self-curing system. In another embodiment, the compound that will react with the bicyclic-containing compound can be a suitable crosslinker. The composition is subjected to suitable conditions to facilitate the necessary reactions and form a cured article.

The crosslinker can be chosen from any suitable material capable of crosslinking siloxane materials. As crosslinkers, any siloxane (co)polymer with hydride groups or with vinyl groups can be used in a method of the present invention, for an addition-cured article. The method of curing depends on the complementary composition of the polymer that is to be crosslinked. For example, co-polymers of methyl hydrosiloxane and phenyl methylsiloxane, copolymers of methyl hydrosiloxane and diphenylsiloxane, and co-polymers of methyl vinylsiloxane and phenyl methylsiloxane and/or combinations of such compounds can be used. In addition, monomeric crosslinkers such as e.g. tetrakis (dimethylsiloxy) silane, dimethylsilane, methylsilane and/or 1,1,3,3-tetramethyl disiloxane can be used as a cross-linking reagents. Alternative cross-linking systems can also be used. In one embodiment, the cross-linking agent can be an unsaturated bicyclic-modified siloxane. A non-limiting example of a suitable bicyclic group attached to silicon would be a norbornene-functional siloxane, which includes the cyclosiloxane of Formula 13 ($D_aD^{\ddagger}_{b'}D^{vi}_j$) where D is shown here where the unsaturated bicyclic containing repeat unit contains norbornene-methyl:

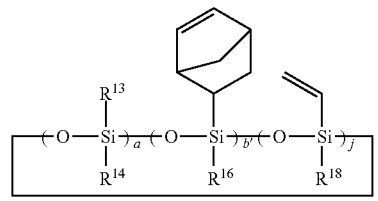

where $R^{13}$, $R^{14}$, $R^{16}$, and $R^{18}$ are previously described and a is 0 to 4 and b' is 1 to 6, j is 0 to 4. In one embodiment of the formula 13 the different substituents such as $R^{13}$, $R^{14}$, $R^{16}$, and $R^{18}$ are all methyl group, a is 0, b' is 2 to 4, and j is 0 to 4 (Formula 13a).

Another non-limiting example of suitable bicyclic-containing siloxane crosslinker includes the cyclo-siloxane of Formula 14 ($D_aD^{\dagger}_bD^{\$}_{b''}$):

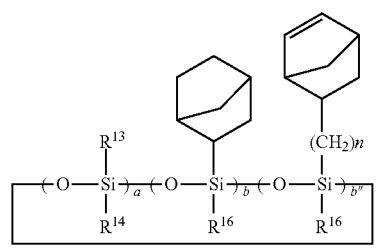

where $D^{\dagger}$ is a bicyclic compound of Formula 1 (shown here as a norbornyl siloxane), $D^{\$}$ is ethylnorbornene-methyl siloxane, $R^{13}$, $R^{14}$, and $R^{16}$ as described before, and n is 0-6. The repeat units a is 0 to 4 and b is 1 to 4, b" is 1 to 6. In one embodiment of formula 14 the various substituents such as $R^{13}$, $R^{14}$, and $R^{16}$ are methyl groups and a is 0, b is 1 to 4 and b" is 1-6 (Formula 14a). In one embodiment, n is 2.

The composition can be cured, for example, by exposing the composition to elevated temperatures. In one embodiment, the composition can be exposed to temperatures of from about 20° C. to about 180° C. The article can be formed to a desired shape by curing in a mold.

The cured articles exhibit excellent properties making them suitable for a variety of applications. In one embodiment, the cured article has a refractive index of from about 1.41 to about 1.61; from about 1.42 to about 1.56; even from about 1.43 to about 1.51. In one embodiment, the cured article has a refractive index of about 1.45. The cured article can have excellent transparency, low gas permeability, desired hardness, etc. In one embodiment, the cured article has a transparency of about 85% or greater; about 90% or greater; about 95% or greater, about 97.5% or greater, or even about 99% or greater. In one embodiment, the cured article has an oxygen permeability of a 1 mm thick sheet of about 50 cm³/m².24 h. atm or greater; about 100 cm³/m².24 h. atm, 200 cm³/m².24 h. atm, or greater; even about 500 cm³/m².24 h.atm or greater. In one embodiment, the cured article can have a hardness of about A10 to about D70; from about A20 to about D60; even from about A50 to about D60. Here as elsewhere in the specification and claims, numerical values can be combined to form new and non-disclosed ranges.

The modified silicone material can be used to make a variety of materials for a variety of applications. The modified silicone material in accordance with aspects of the invention can be used to form coatings or films that can be applied to the surface of other materials or that can be used to form products of a desired shape. The modified silicone material and polymers formed therefrom can exhibit relatively high refractive indexes and excellent mechanical properties and also avoid other problems associated with polymers comprising phenyl groups as the high refractive index component. The present polymers can be used in a variety of applications including, but not limited to, contact lenses, intraocular lenses solid state lighting encapsulants (light emitting diodes, organic light emitting diodes, laser diodes), waveguides (both planar and "fiber" geometries), optical computing, optical storage media, antireflection coatings, conformal coatings, optical lenses, microlenses, automobile topcoats, paint formulations and topcoats, personal care products, e.g, color cosmetics and hair care products, gradient refractive index optical components, dynamic gradient refractive index components, etc.

The modified silicone material and polymers formed therefrom can be used in a composition or formulation suitable for producing a composition or material useful for the desired application. Such compositions or formulations may include a suitable carrier, filler, additive, etc. or other materials to provide a suitable material.

The modified silicone material comprising the bridged bicyclic group can be employed as a compatibility modifier in certain applications. Phenyl silicones are used in a variety of compositions such as cosmetics/personal care products, encapsulants, lubricants, liquid crystal compositions, sealants, etc. The modified silicone material with the bridged bicyclic group may be more compatible with various formulation ingredients than other conventional materials such as phenyl-containing silicone compositions. The present materials can be used as an alternative to phenyl silicone or used in combination with phenyl silicone.

In one embodiment, the modified silicone material can be included in a personal care composition such as, but not limited to, cosmetics, sunscreen, hair products such as shampoo or conditioner, lotions, creams, etc. Personal care compositions can include various ingredients such as a carrier, pigment, film formers, emulsifiers, vitamins, plasticizers, surfactants, antioxidants, waxes, oils, solvents, etc.

In one embodiment, a personal care product may optionally contain 0-90 parts by weight pigments. Pigments suitable for use herein are all inorganic and organic colors/pigments. These are usually aluminum, barium or calcium salts or lakes. Lakes are either a pigment that is extended or reduced with a solid diluent or an organic pigment that is prepared by the precipitation of a water-soluble dye on an adsorptive surface, which usually is aluminum hydrate. A lake also forms from precipitation of an insoluble salt from an acid or basic dye. Calcium and barium lakes are also used herein. Suitable lakes include, but are not limited to, Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake. Other colors and pigments can also be included in the compositions, such as pearls, titanium oxides, Red 6, Red 21, Blue 1, Orange 5, and Green 5 dyes, chalk, talc, iron oxides and titanated micas.

A personal care composition may optionally contain 0-99 parts by weight organic film former known in the prior arts. The film-forming agent may be any which is cosmetically acceptable. Examples of useful film-forming agents include natural waxes, polymers such as polyethylene polymers, and copolymers of PVP, ethylene vinyl acetate, dimethicone gum, and resins, such as shellac, polyterpenes.

A personal care composition may optionally include 0-50 parts by weight either blocking or absorbing sunscreening agents. Blocking sunscreening agents are generally inorganic, such as various cesium oxides, chromium oxides, cobalt oxides, iron oxides, red petrolatum, silicone- and other treated titanium dioxides, titanium dioxide, zinc oxide, and/or zirconium oxide, $BaTiO_3$, $CaTiO_3$, $SrTiO_3$ and SiC. Absorbing sunscreening agents, which are usually organic species, are particularly useful. Such absorbing sunscreening agents include, but are not limited to, UV-A absorbers, which generally absorb radiation in the 320 to 400 nm region of the ultraviolet spectrum, for example anthranilates, benzophenones, and dibenzoyl methanes; and UV-B absorbers, which generally absorb radiation in the 280 to 320 nm region of the ultraviolet spectrum, for example, p-aminobenzoic acid derivatives, camphor derivatives, cinnamates, and salicylates. Specific examples of organic sunscreening agents include p-aminobenzoic acid, avobenzone cinoxate, dioxybenzone, homosalate, menthyl anthranilate, octocrylene, octyl methoxycinnamate, octyl salicylate, oxybenzone, padimate, phenylbenzimidazole sulfonic acids, sulisobenzone, trolamine salicylate, aminobenzoic acid, amyldimethyl p-aminobenzoic acid, diethanolamine p-methoxycinnamate, digalloyl trioleate, 2-ethylhexyl-2-cyano-3,3-diphenylacrylate, ethylhexylp-methoxycinnamate, 2-ethylhexyl salicylate, glyceryl aminobenzoate, homomenthyl salicylate, homosalate, 3-imidazol-4-ylacrylic acid and the ethyl ester thereof, methyl anthranilate, octyldimethyl PABA, 2-phenylbenzimidazole-5-sulfonic acid and salts, sulisobenzone, triethanolamine salicylate, N,N,N-trimethyl-4-(2-oxoborn-3-ylidene methyl)anillinium methyl sulfate, aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammonium)-benzyliden-boman-2-one methylsulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4'dimethoxybenzophenone, 2-hydroxy-4-n-octoxybenzophenone, 2-hydroxy-4-methoxy-4'-methoxybenzophenone, ca-(2-oxoborn-3-ylidene)-tolyl-4-sulfonic acid and soluble salts thereof, 3-(4'-sulfo) benzyliden-bornan-2-one and soluble salts thereof, 3-(4'-methylbenzylidene)-d,l-camphor, 3-benzylidene-d,l-camphor, benzene 1,4-di(3-methylidene-10-camphosulfonic) acid and salts thereof, urocanic acid, 2,4, 6-tris-(2'-ethylhexyl-1'-oxycarbonyl)-anilinol 1,3,5-triazine, 2-(p-(tert-butylamido)anilinol-4,6-bis-(p-(2'-ethylhexyl 1'-oxycarbonyl) anilinol 1,3,5-triazine, 2,4-bis{1,4-(2-ethylhexyloxy)-2-hydroxyl-phenyl}-6-(4-methoxyphenyl)-1,3,5-triazine, the polymer of N-(2 et 4)-(2-oxoborn-3-yliden) methylbenzyl acrylamide, 1,4-bisbenzimidazolyl-phenylen-3,3',5,5'-tetrasulfonic acid and salts thereof, the benzalmalonate-substituted polyorganosiloxanes, the benzotriazole-substituted polyorganosiloxanes (Drometrizole Trisiloxane), solubilized 2,2'-methylene-bis-1,6-(2H-benzotriazol-2-yl)-4-(1,1,3,3-tetramethylbutyl) phenol, 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'- methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane, and combinations comprising at least one of the foregoing sunscreening agents.

A personal care composition can be specifically formulated for use as, but not limited to, a color cosmetic, sunscreen, hair conditioner, a moisturizer, etc. Suitable forms and formulations for such application are known to those of ordinary skill in the art. For example, when formulated for use as a sunscreen, the composition may be in the form of a lamellar emulsion, a mirocoemulsion, or a nanoemulsion. In addition, the emulsions may be a fluid simple emulsion, a fluid multiple emulsion, a rigid simple emulsion, or a rigid multiple emulsion. The simple emulsion or multiple emulsion may comprise a continuous aqueous phase containing dispersed lipid vesicles or oil droplets, or a continuous fatty phase dispersed lipid vesicles or water droplets. In one embodiment, the sunscreen application is an emulsion having a continuous aqueous phase, and may be in the form of a stick, a lotion, a gel, a spray, and the like. Suitable emulsifiers for the formation of sunscreen emulsions include, for example ethoxylated surfactants known in the art such as Polysorbate-20, Laureth-7, Laureth-4, Sepigel® 305 available from SEPPIC, oils such as vegetable and mineral oil; animal and/or synthetic waxes such as beeswax, paraffin, rice bran wax, candelilla wax, carnauba wax and derivatives thereof; and hydrocarbon gels or bentone type gels, such as Gel SS71, Gel EA2786, Quaternium-18 Bentonite, 38 CE, Gel ISD V or Gel ISD; and organosilicone emulsifiers such as cetyl dimethicone copolyol-polyglyceryl4-isostearate-hexylaurate (ABIL® WE 09) available from Goldschmidt Chemical Corporation, behenate dimethicone, cetyl dimethicone copolyol (ABIL® EM 90), (ABIL® EM 97), laurylmethicone copolyol (5200), cyclomethicone and dimethicone copolyol (DC 5225 C and DC 3225 C), cyclopentasiloxane and dimethicone copolyol (SF 1528).

A personal care composition may optionally contain vitamins or skin nourishing agents. Some suitable agents are ceramides, hyaluronic Acid, panthenol, peptides (copper hexapeptide-3), AHA's (lactic acid), retinols (retinyl palmitate)-Vit. A derivatives, vitamin C (1-ascorbic acid), BHA's (salicylic Acid), teas (Green Tea, White Tea, Red Tea), soy and other plant derivatives, isoflavones (Grape Seed Extract), argireline, acai berry.

Plasticizers may also be added to the formulation to improve the flexibility and cosmetic properties of the resulting formulation. Plasticizers are frequently used to avoid brittleness and cracking of film formers, and include, for example, lecithin, polysorbates, dimethicone copolyol, glycols, citrate esters, glycerin, and dimethicone. One skilled in the art may routinely vary the amount of plasticizer desired based on the properties desired and the application envisaged.

The composition of the present invention can be incorporated into a carrier, such as a volatile carrier which quickly volatilizes after application. The volatile carriers can be selected from volatile hydrocarbons, volatile silicones, and mixtures thereof.

Hydrocarbon oils useful in personal care products include those having boiling points in the range of 60-260° C., including hydrocarbon oils having from about $C_8$ to about $C_{20}$ chain lengths, even $C_8$ to $C_{20}$ isoparaffins. Examples include isododecane, isohexadecane, isoeocosane, 2,2,4-trimethylpentane, 2,3-dimethylhexane, and mixtures of two or more thereof.

Suitable volatile silicone fluids include cyclomethicones having 3, 4 and 5 membered ring structures corresponding to the formula $(R_2SiO)_x$, where x is from about 3 to about 6.

These and other aspects and embodiments of the invention are further illustrated with reference to the following Examples. The Examples are merely for the purpose of illustrating aspects of the invention and are not intended to limit the invention to the specific aspects illustrated therein.

EXAMPLES

Example 1—Synthesis of Cyclic Siloxane, 2b

Norbornyl cyclic siloxane of formula 2b is synthesized in accordance with aspects of Synthesis Scheme 5:

Scheme 5: Synthesis of 2b

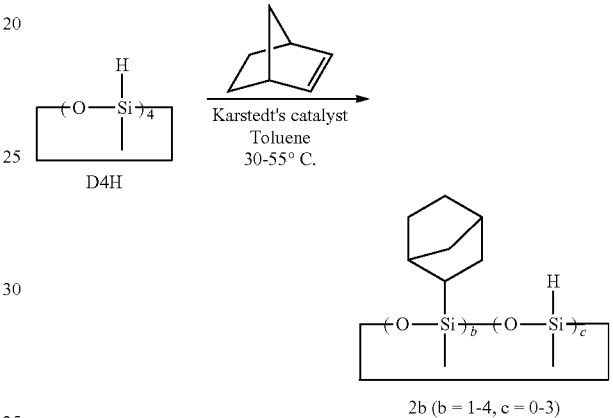

2b (b = 1-4, c = 0-3)

A 125-mL three-necked round-bottomed flask equipped with an addition funnel, a reflux condenser, magnetic stirrer, J-KEM, nitrogen inlet/outlet, and a TCU is charged with $D^H_4$ (15 g, 62.4 mmol, 1 equiv) in toluene (15 mL, 1 vol). The batch is maintained at 30±5° C. A solution of norbornene (11.9 g, 126 mmol, 2.02 equiv) and Karstedt's catalyst (2.38 mg, 62.4 mg of a 0.1 M solution in PDMS) in toluene (15 mL, 1 vol) is added drop wise at a rate such that the bath temperature remains 30±5° C. Once the addition is complete, the bath is held at 30±5° C. for 1 hour followed by at 45±5° C. for 2 hours. The batch is now cooled to 20±5° C. Silica gel (3.0 g, 20 wt %) is added to the batch and the solution is stirred for 1 hour and then filtered. The silica gel is washed with hexanes (1×7.5 mL, 1×0.5 vol). The combined filtrate is stirred with charcoal (1.5 g, 10 wt %) for 2 hours. The batch is filtered and the charcoal layer is washed with hexanes (1×7.5 mL, 1×0.5 vol). The combined filtrate is concentrated and dried at high vacuum (<2 millibar g 70° C.) for 2 hours. The fluid is filtered through a 0.45 micron syringe filter to obtain a colorless fluid (2b, 22.1 g, 83%, $n_D$ 1.46, lot #4161-75-02). The analytical data ($^1$H NMR, $^{13}$C NMR, $^{29}$Si NMR, MS) correspond to the composition 2b.

Example 2—Synthesis of Cured Article

A vial is charged with the cyclic siloxane of Example 2b (1 g, 2.33 mmol, 1 equiv), $D^{vi}_4$ (0.402 g, 1.17 mmol, 0.5 equiv), Irganox 3114 (3.92 mg, 0.005 mmols, 0.002 equiv), and Karstedt's catalyst (0.09 mg, 47 mg of 5 wt % toluene solution of 0.1 M Karstedt's in PDMS). The fluid was mixed and then degassed via sonication. The fluid is then poured into a 1"×1"×0.2 mm Teflon mold. The mold is transferred into an oven and fluid is cured for 1.5 hours at 150° C. The mold is then cooled to ambient before taking out the cured article from the mold.

The gas permeability of the cured article is evaluated using differential pressure method JIS K7126-1. The method is conducted using a MT-C3 tester from Toyo Seiki Seisakusho, Ltd. The temperature is 23° C., the humidity is 0%, and the test gas is 100% oxygen. Table 1 compares the gas permeability of the cured article of Example 2 to commercially available methyl and phenyl silicones.

TABLE 1

| Sample | $O_2$ permeation rate $(cm^3/m^2 \cdot 24 \text{ hours} \cdot atm)$ | Thickness (mm) |
| --- | --- | --- |
| Example 2 | 524 | 0.906 |
| phenyl silicone 1 | 703 | 1.005 |
| methyl silicone 1 | 33100 | 1.021 |
| methyl silicone 2 | 36400 | 1.012 |

As illustrated in Table 1, the cured article derived from a norbornane modified siloxane exhibits superior barrier performance as noted in the lower gas permeability compared to conventional methyl and phenyl siloxanes.

Examples 3 and 4—Synthesis of Norbornane Methyl Siloxane Copolymer

Norbornane methyl siloxane copolymers are synthesized in accordance with aspects of Synthesis Scheme 6:

Scheme 6: Synthesis of 11a and 11b

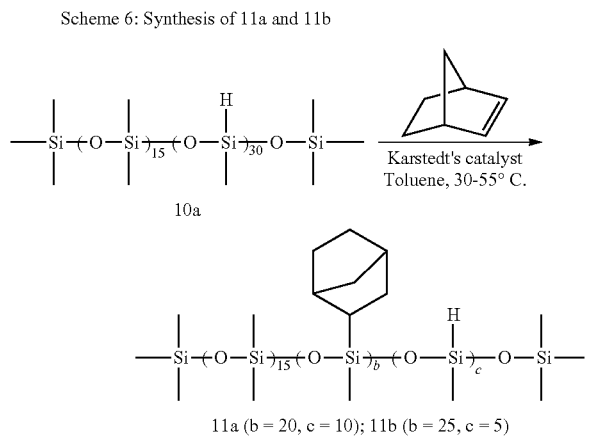

11a (b = 20, c = 10); 11b (b = 25, c = 5)

The reactions are controlled such that the norbornyl methyl siloxane copolymer of Example 3 (11a) has b=20 and c=10, and the norbornane methyl siloxane copolymer of Example 4 (11b) has b=25 and c=5.

Example 3 (11a) is prepared as follows: A 250-mL three-necked round-bottomed flask equipped with an addition funnel, a reflux condenser, magnetic stirrer, J-KEM, nitrogen inlet/outlet, and a TCU is charged with 10a (20 g, 6.50 mmol, 1 equiv) in toluene (20 mL, 1 vol). The batch is maintained at 30±5° C. A solution of norbornene (12.2 g, 130 mmol, 20.0 equiv) and Karstedt's catalyst (4.95 mg, 130 mg of a 0.1 M solution in PDMS) in toluene (20 mL, 1 vol) is added drop wise at a rate such that the bath temperature remains 30±5° C. Once the addition is complete, the bath is held at 30±5° C. for 1 hour followed by heating at 55±5° C. for 4 hours. The batch is concentrated on a rotatory evaporator (@70±5° C. and =10 torr). Toluene (2×20 mL, 2×2 vol) is co-distilled. The final bath is then dried under high vacuum (70±5° C. @ 1-2 millibar) for 2 hours to obtain a clear liquid (11a, 32.2 g, ~99%, $n_D$ 1.465). The desired product is confirmed by analytical data ($^1$H NMR, $^{13}$C NMR, and $^{29}$Si NMR).

Example 4 (11b) is prepared in a similar manner to that of Example 3 except that a solution of 10a (20 g, 6.50 mmol, 1 equiv) in toluene (20 mL, 1 vol) is reacted with a solution of norbornene (15.3 g, 162 mmol, 25.0 equiv) and Karstedt's catalyst (4.95 mg, 130 mg of a 0.1 M solution in PDMS) in toluene (20 mL, 1 vol) to prepare as a clear colorless oil (11b, 36 g, ~99%, $n_D$ 1.477). The desired product is confirmed by analytical data ($^1$H NMR, $^{13}$C NMR, and $^{29}$Si NMR).

Example 5—Synthesis of Norbornane Cyclic Siloxane 2a

A norbornane cyclic siloxane of the Formula 2a is prepared according to Scheme 7:

Scheme 7: Synthesis of 2a

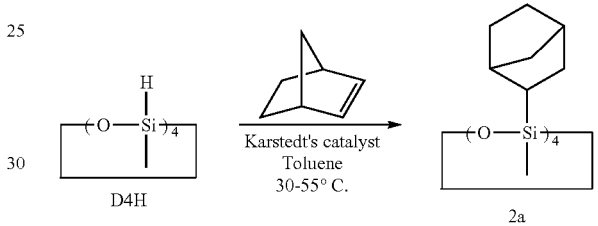

A 125-mL three-necked round-bottomed flask equipped with an addition funnel, a reflux condenser, magnetic stirrer, J-KEM, nitrogen inlet/outlet, and a TCU is charged with $D^H_4$ (10 g, 41.6 mmol, 1 equiv) in toluene (10 mL, 1 vol). The batch is maintained at 45±5° C. A solution of norbornene (15.9 g, 168 mmol, 4.05 equiv) and Karstedt's catalyst (3.17 mg, 83.2 mg of a 0.1 M solution in PDMS) in toluene (10 mL, 1 vol) is added drop wise at a rate such that the bath temperature remains at 45±5° C. Once the addition is complete, the bath is held at 45±5° C. for 1 hour followed by heating at 55±5° C. for 2 hours. The batch is concentrated on a rotatory evaporator (@70±5° C. and ~10 torr). Toluene (2×20 mL, 2×2 vol) is co-distilled. The final bath is then dried under high vacuum (70±5° C. 1-2 millibar) for 2 hours to obtain a clear thick oil (2a, 26.0 g, ~99%, $n_D$ 1.499). The desired product is confirmed by analytical data ($^1$H NMR, $^{13}$C NMR, $^{29}$Si NMR, and MS).

Example 6—Synthesis of Vinyl Terminated Norbornane-Methyl Siloxane copolymer 6a ($D^{vi}_j=0$)

A vinyl terminated norbornyl-methyl siloxane copolymer is prepared via a reaction in accordance with Scheme 8 to create $M^{vi}D_{350}D^{\dagger}_{90}M^{vi}$, where $D^{\dagger}$ is norbornyl-methyl siloxane:

Scheme 8: Synthesis of 6a

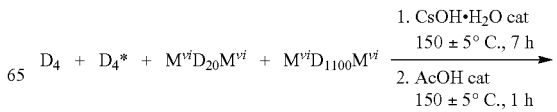

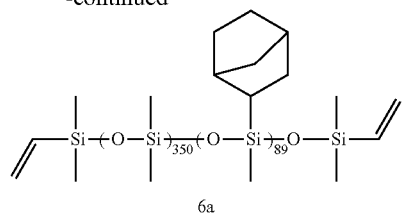

6a

A 250 mL-three-necked round-bottomed flask equipped with a distillation set up, mechanical stirrer, J-KEM, and nitrogen inlet/out let is charged with chain stopper $M^{vi}D_{20}M^{vi}$ (4.26 g, 2.55 mmol, 1 equiv), $D_4$ (60 g, 250 mmol, 98 equiv), the norbornane cyclic siloxane $D^\dagger_4$ from Example 5 (2a, 29.6 g, 68.9 mmol, 27 equiv), and seed polymer, $M^{vi}D_{1100}M^{vi}$ (3.13 g, 0.04 mmol). The batch is heated to 140° C. About 6 mL of the distillate is collected under a gentle stream of nitrogen. The batch is then cooled to 50±5° C. Catalytic amount of $CsOH \cdot H_2O$ (10 mg, 0.0001 equiv) is added and the batch is aged at 150±5° C. for 7 hours. A catalytic amount of acetic acid (2 drops, 14 mg) is added to the reaction mixture which is then aged at 150±5° C. for 1 hour. The batch is subjected to stripping (160±5° C. @ 1 mm of vacuum). Once stripping is complete (no distillate observed), the batch is cooled to room temperature and filtered through a 0.45 micron filter to obtain a clear colorless oil (6a, 82 g, 85%, $n_D$ 1.439). The product is confirmed by analytical data ($^1$H NMR and $^{29}$Si NMR).

Example 7—Synthesis of a Linear Norbornyl-phenyl-methyl Siloxane Via Equilibration A linear norbornyl-phenyl-methyl siloxane was prepared according to Scheme 9 and Table 2:

Scheme 9

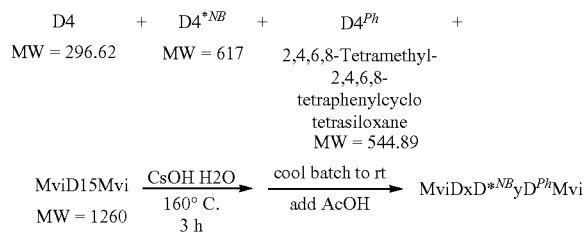

TABLE 2

| chemicals | MW | QTY | Moles | Equiv. |
|---|---|---|---|---|
| D4 | 296.62 | 22.83 g | 0.0793650 | 100 |
| D4*NB | 617 | 4.89 g | 0.00793650 | 10 |
| D4Ph | 544.89 | 4.324 g | 0.00793650 | 10 |
| MviD15Mvi | 1260 | 1 g | 0.0007936 | 1 |
| CsOH•H2O | 167.93 | 0.100 g | Wt % | cat |
| AcOH | 60 | | Wt % | cat |

A 250 mL three-necked round-bottomed flask equipped with a distillation set up, mechanical overhead stirrer, and nitrogen inlet/out let was charged with D4, D4*$^{NB}$, D4$^{Ph}$ and $M^{vi}D_{15}M^{vi}$ (chain stopper) and cat. $CsOH \cdot H_2O$. The batch was brought to 160° C. and maintained until the process is complete. In 3 hours, the reaction mixture turned hazy with apparent viscosity increase. The reaction was followed by $^1$H NMR, moisture analyzer, and GPC. Moisture (solid content) analyzer after 3 hours is 82% (150° C., 20 min).

Example 8—Linear Norbornyl-epoxy Siloxane

A linear norbornyl-epoxy siloxane was prepared according to Scheme 10 and the formulations in Table 3:

Scheme 10

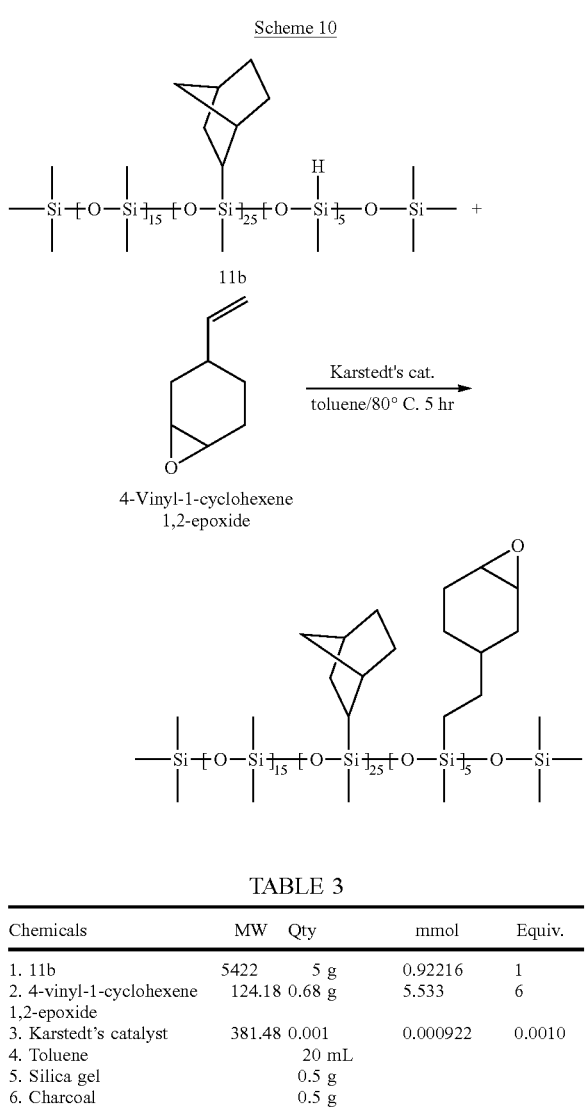

11b

4-Vinyl-1-cyclohexene 1,2-epoxide

Karstedt's cat.
toluene/80° C. 5 hr

TABLE 3

| Chemicals | MW | Qty | mmol | Equiv. |
|---|---|---|---|---|
| 1. 11b | 5422 | 5 g | 0.92216 | 1 |
| 2. 4-vinyl-1-cyclohexene 1,2-epoxide | 124.18 | 0.68 g | 5.533 | 6 |
| 3. Karstedt's catalyst | 381.48 | 0.001 | 0.000922 | 0.0010 |
| 4. Toluene | | 20 mL | | |
| 5. Silica gel | | 0.5 g | | |
| 6. Charcoal | | 0.5 g | | |

A 100 mL three-necked round-bottomed flask equipped with an addition funnel, a reflux condenser, nitrogen inlet/outlet was charged with compound 11b in toluene (10 mL). A solution of 2,4-vinyl-1-cyclohexene 1,2-epoxide in toluene (10 mL) and Karstedt's catalyst was added drop wise at temperature remained 70° C. Once the addition was completed, the bath was held at 80° C. for 5 hours. The reaction was followed by $^1$H NMR.

An additional 8 equivalents (7.377 mmol, 0.91 g) of a 4-vinyl-1-cyclohexene 1,2-epoxide was added in the reaction to complete the reaction to the maximum extent. The batch was brought to room temperature and then stirred with silica gel and charcoal for 1 hour. The batch was filtered; silica and charcoal were washed with toluene (20 mL). The combined filtrate was concentrated and dried under high vacuum which afforded 5.7 g of product. RI=1.483 (at 25° C.). The epoxy modified compounds can provide a material that is thermal curable, photo curable, or amine curable.

Example 9—Linear Norbornyl-silyloxy Siloxane

A linear norbornyl-silyloxy siloxane was prepared according to Scheme 11 and Table 4

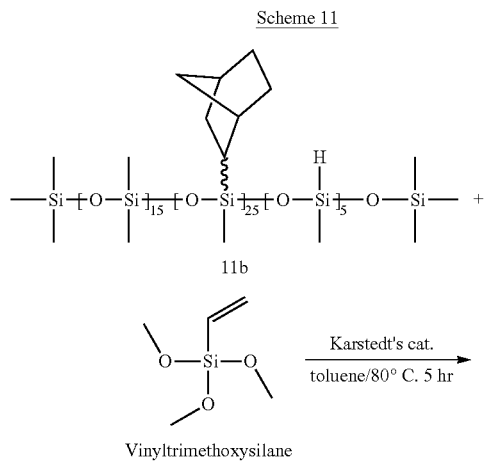

TABLE 4

| Chemicals | MW | Qty | mmol | Equiv. |
|---|---|---|---|---|
| 1. 11b | 5422 | 5 g | 0.92216 | 1 |
| 2. Vinyltrimethoxysilane(VTMS) | 148.23 | 0.82 g | 5.53301 | 6 |
| 3. Karstedt's catalyst | 381.48 | Cat. | | Cat. |
| 4. Toluene | | 20 mL | | |

A 100 mL three-necked round-bottomed flask equipped with an addition funnel, a reflux condenser, nitrogen inlet/outlet was charged with compound 11b in toluene (10 mL). A solution of 2, vinyltrimethoxysilane (VTMS) in toluene (10 mL) and Karstedt's catalyst was added drop wise at temperature remained 50° C. Once the addition was completed, the bath was held at 80° C. for 2 hours. The reaction was followed by 1H NMR. Additional 8 equivalents (7.377 mmol, 1.09 g) of VTMS were added in the reaction to complete the reaction to the maximum extent. RI nD=1.465 (at 23° C.). The silyloxy material can be useful in condensation curing reactions.

Example 10—Condensation Curing of a Linear Norbornyl-silyloxy Siloxane

A linear norbornyl-silyloxy siloxane was prepared according to Scheme 12:

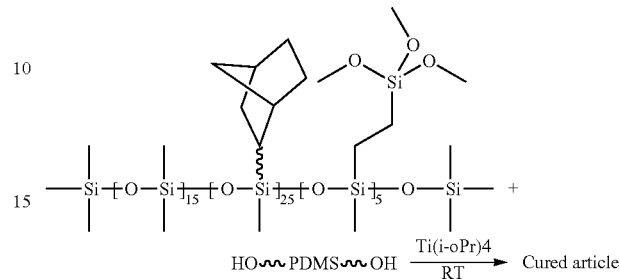

The condensation-curing of a linear norbornyl-silyloxy siloxane was studied using Ti(i-OPr)$_4$ as a catalyst. The linear norbornyl-silyloxy siloxane (1 g), OH-PDMS-OH (1 g) was mixed with Ti(i-OPr)$_4$ catalyst (0.04 g) and exposed to air. The curing was followed by the tack free time (TFT) observation. The TFT was 20-25 min. The hardness of the cured article was Shore A22.

Example 12—Self-Condensation Curing of a Linear Norbornyl-silyloxy Siloxane

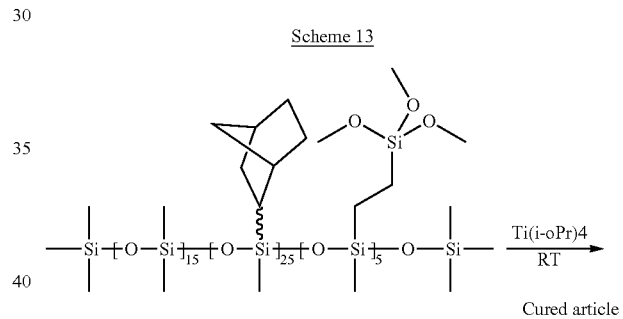

The self-condensation-curing of a linear norbornyl-silyloxy siloxane was initiated using Ti(i-OPr)4 as a catalyst. The linear norbornyl-silyloxy siloxane (1 g) was mixed with Ti(i-OPr)4 catalyst (0.03 g) and exposed to air. The curing was followed by the tack free time (TFT) observation. The TFT was overnight. The hardness of a cured article was Shore A20.

Example 13—Self Condensation Curing of a Linear Norbornyl-silyloxy Siloxane

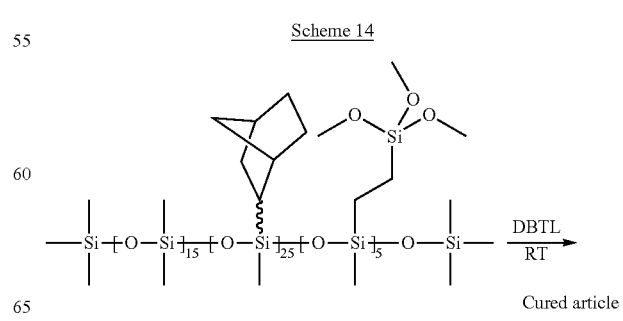

The self-condensation-curing of a linear norbornyl-silyloxy siloxane was initiated using DBTL as a catalyst. The linear norbornyl-silyloxy siloxane (1 g) was mixed with DBTL catalyst (0.03 g) and exposed to air. The curing was followed by the tack free time observation. The TFT was 10-15 min.

Self-condensation curing of a linear norbornyl-silyloxy siloxane was faster in the case of DBTL as a catalyst as compared to Ti(i-OPr)4 catalyst.

The hardness of a cured article could not be evaluated because it exceeded the Shore A scale and exhibited brittle fracture.

Example 14—Norbornyl MQ Resin 1

This example describes the formation of a well-defined $M^\dagger_4Q$ structure. $M^\dagger_4Q$ was prepared as follows. A round bottom flask was charged Pt(COD)Cl2 (1.5 mg, 11 ppm Pt), and norbornene (64.4 g, 0.68 Mol). The solids were heated to 50° C. and the Norbornene melted into a light yellow oil. The $M^H_4Q$ silane (Tetrakis(dimethylsiloxy)silane) (55.0 g, 0.17 Mol) was added via addition funnel. After confirmation of an exotherm, the silane addition was continued at a rate to keep the reaction temperature at around 70° C. After completion of the addition of the silane the reaction mixture was allowed to stir at 60° C. for 90 minutes. The reaction mixture was then placed on a rotory evaporator for 60 minutes at 50° C. and a pressure of 50 torr. The resulting product was transferred to a pre-tared vial while still at temperature isolating product as a clear oil. The product was confirmed by $^1$H and $^{29}$SiNMR.

Example 15—Norbornyl MQ Resin 2

$M^\dagger_6Q_2$ was prepared as follows. A round bottom flask was charged Pt(COD)Cl$_2$ (1.2 mg, 10 ppm Pt), and norbornene (53.4 g, 0.56 Mol). The solids were heated to 50° C. and the Norbornene melted into a light yellow oil. The $M^H_6Q_2$ silane resin (60.0 g, 0.11 Mol) was added via addition funnel. After confirmation of an exotherm, the silane addition was continued at a rate to keep the reaction temperature around 70° C. After completion of the addition of the silane, the reaction mixture was allowed to stir at 60° C. for 90 minutes. The reaction mixture was then placed on a rotory evaporator for 60 minutes at 50° C. and a pressure of 50 torr. The resulting product was transferred to a pre-tared vial while still at temperature isolating product as a hazy oil. The product was confirmed by $^1$H and $^{29}$SiNMR.

Example formulations containing M*Q resins: Commercial formulations of color cosmetic lipsticks, lipstains, and lipglosses were purchased and formulated with the $M^\dagger_4Q$ resin (of example 5). 1 g of each formulation was melted at 80 C for 30 minutes and added 0.02 g (2 wt %) of the $M^\dagger_4Q$ resin. The mixture was mixed in a Hauschield speedmixer for 60 seconds. The formulation was wiped in a Hegman Grind gauge and the gloss was measured using a microgloss meter at 60 degrees. The performance of these formulations is provided in Table 5 below:

TABLE 5

| Manufacturer Brand | Loreal Colour Riche | Loreal Infallible | Revlon Super Lustrous | CoverGirl Continuous Color | Revlon ColorStay Ultimate |
|---|---|---|---|---|---|
| Product Color # | 815 | 741 | 845 | 430 | 040 |
| 60° Gloss | 9.3 | 5.7 | 37.3 | 11.3 | 50.2 |
| 60° Gloss w/M$^\dagger_4$Q | 34.3 | 38.3 | 44.2 | 13.6 | 45.2 |

Aspects of the invention may be further understood with respect to the following examples. The examples are for the purpose of illustrating various aspects and embodiments of the invention and are not intended to limit the scope of the invention.

What is claimed is:

1. A silicon-containing material modified with a saturated bridged bicyclic group, wherein the silicon-containing material is a cyclic siloxane comprising at least one silicon atom in the siloxane having a saturated bridged bicyclic group attached thereto, the saturated bridged bicyclic group is a bicyclo(2,2,1) group of formula (1):

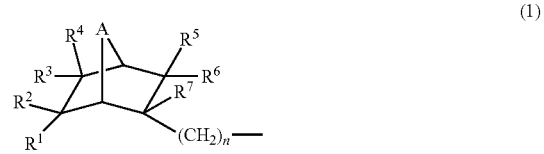

(1)

where $R^1$-$R^7$ are independently chosen from H, a C1-C12 alkyl, —CO$_2$R', and —(CH$_2$)$_n$—B; n is 0-12; B is OR', SR', NR$^1$R$^2$; R' is a C1-C12 alkyl; and A is from CH$_2$, NR', S, SO, or SO$_2$; and the silicon-containing material is a cyclic siloxane of formula (2):

(2)

where $D^{1-3}$ are groups of the formula $R^1R^{14}SiO_{2/2}$, $R^{13}$ and $R^{14}$ are independently chosen from a bicyclic compound of Formula 1, H, an unsubstituted or substituted monovalent hydrocarbon groups, aromatic groups, alkoxy, mercaptopropyl, isocyanyl, and glycidyl groups, where at least one of the $R^{13}$ or $R^{14}$ groups is a bicyclic compound of Formula 1, a+b+c is between 3 and 10, and at least one of a, b, or c is greater than zero, and wherein the silicon-containing material has an aromatic content of from about 0.1 weight percent to about 40 weight percent.

2. The silicon-containing material of claim 1, wherein the bicycle(2,2,1) group of formula 1 is a norbornyl group bonded to a silicon atom.

3. The siloxane of claim 1, wherein the siloxane is of the formula 2a:

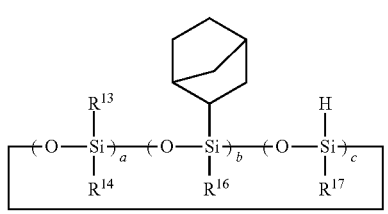

(2a)

where a is from 0-6, b is 1-6, c is 0-6, $R^{13}$, $R^{14}$, and $R^{17}$ are independently chosen from an unsubstituted or substituted monovalent hydrocarbon groups, aromatic groups, alkoxy, mercaptopropyl, isocyanyl, and glycidyl groups; and $R^{16}$ is chosen from a norbornyl or a group as described for $R^{13}$, $R^{14}$, and $R^{17}$.

4. The siloxane of claim 3 where a is 0, b is 1-6, c is 0 and $R^{16}$ methyl group.

5. The siloxane of claim 3 where a is 0, b is 1-4, c is 1-3, and $R^{16-17}$ are methyl groups.

6. The siloxane of claim 3 where a+b+c are between 3-10.

7. The silicon-containing material of claim 1 having a norbornyl content of from about 1 weight percent to about 90 weight percent.

8. The silicon-containing material of claim 1, wherein the siloxane is substantially free of any aromatic groups.

9. A curable composition comprising a silicon-containing material of claim 1 and a compound that will react with the silicon-containing material.

10. The composition of claim 9, wherein the compound that will react with the silicon-containing material is a second silicon-containing material modified with a saturated bridged bicyclic group, the second silicon-containing material being the same or different than the silicon-containing material.

11. The composition of claim 9, wherein the compound that will react with the silicon-containing material is a crosslinker.

12. The composition of claim 11, wherein the crosslinker is chosen from norbornyl-functional siloxanes, cyclosiloxanes, copolymers thereof, or a combination of two or more thereof.

13. The composition of claim 12, wherein the cross-linker is of formula 14

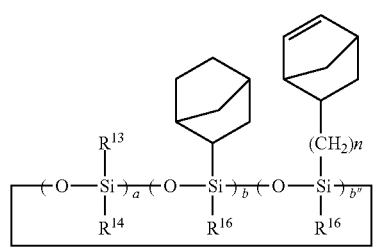

(14)

where $R^{13}$, $R^{14}$, and $R^{16}$ are independently chosen from an unsubstituted or substituted monovalent hydrocarbon groups, aromatic groups, alkoxy, mercaptopropyl, isocyanyl, glycidyl groups, or a combination of two or more thereof; a is 0 to 4, b is 1 to 4, b" is 1 to 6, and n is 0-6.

14. The curable composition of claim 9 further comprising an antioxidant, a thermal stabilizer, a UV stabilizer, an adhesion promoter, a metal catalyst, an inhibitor, a filler, an initiator, or a combination of two or more thereof.

15. The curable composition of claim 14 comprising a platinum group metal catalyst, a ruthenium group metal catalyst, or a combination thereof, the catalyst being present in a concentration of about 1 to about 100 ppm.

16. The composition of claim 9, wherein the curable composition is UV curable, condensation curable, amine curable, thermal curable, or a combination of two or more thereof.

17. A cured article formed from the composition of claim 9.

18. The cured article of claim 17 having a refractive index of from about 1.42 to about 1.55.

19. The cured article of claim 17 having a transparency of ≥90% of a 1 mm thick sheet.

20. The cured article of claim 17 having a gas permeability of from about 100 to 10000 $cm^3/m^2$.24 h. atm.

21. The cured article of claim 17, where the articles are used as LED encapsulants, optical waveguides, optical lenses, optical bonding materials, optical adhesives, optical films or sheets, laminated films or sheets, in electronic components, or in combination with semiconductor devices.

* * * * *